United States Patent [19]
Heitz

[11] Patent Number: 5,876,409
[45] Date of Patent: Mar. 2, 1999

[54] IMPLEMENT AND METHOD FOR REMOVING TICKS FROM SKIN

[76] Inventor: Denis Heitz, rue de l'Epine, Lavancia-Epercy, France, 01590

[21] Appl. No.: 913,767
[22] PCT Filed: May 30, 1996
[86] PCT No.: PCT/FR96/00812
  § 371 Date: Sep. 23, 1997
  § 102(e) Date: Sep. 23, 1997
[87] PCT Pub. No.: WO96/38095
  PCT Pub. Date: Dec. 5, 1996

[30] Foreign Application Priority Data

May 31, 1995 [FR] France .................................. 95 06557

[51] Int. Cl.⁶ .................................................. A61B 17/50
[52] U.S. Cl. ............................................. 606/131; 173/90
[58] Field of Search ............................... 606/131; 173/90

[56] References Cited

U.S. PATENT DOCUMENTS 2,021,007  11/1935  Holland .
5,116,347   5/1992  Butler .
5,246,449   9/1993  Webster .
5,595,569   1/1997  Hebbard ................................. 606/131
5,607,434   3/1997  Alvino ................................... 606/131

FOREIGN PATENT DOCUMENTS 94561   5/1983  European Pat. Off. .
520169  12/1919  France .
2166681  5/1986  United Kingdom .

*Primary Examiner*—Michael Buiz
*Assistant Examiner*—Tan-Uyen Thi Ho
*Attorney, Agent, or Firm*—Dowell & Dowell, P.C.

[57] ABSTRACT

Implement for removing parasitic ticks from the skin of animals or humans, characterized in that it is a one-piece device comprising a handle (3) ending in a grip portion (1,2) of circular cross-section, and a curved and flattened end with a forked tip (4) substantially perpendicular to the rotation axis of the grip (1,2), said forked tip (4) having two tines (5) defining an inter-tine (6) gap for gripping the tick, wherein the implement is capable of removing the tick by rotating about an axis substantially perpendicular to the plane of the skin to which it is attached.

12 Claims, 3 Drawing Sheets

IMPLEMENT AND METHOD FOR REMOVING TICKS FROM SKIN

BACKGROUND OF THE INVENTION

1. Field of the Invention

The present invention relates to an instrument intended to remove parasitic ticks from the skin of animals or man, in particular from pets or live-stock.

2. Description of the Related Art

Ticks, whether in their larvae, pupa or adult state, adhere to the skin owing to a rostrum that penetrates the epidermis. Traditionally, these ticks are removed with ether and tweezers of various designs, but it frequently happens that the tick's head and rostrum remain embedded in the skin.

Certain tweezers enable the removal of ticks without first using ether, but their design is quite complex, while their manner of gripping the tick, by squeezing its body, contributes to the regurgitation of blood and saliva towards the skin of the animal and thus the transmission of certain diseases.

SUMMARY OF THE INVENTION

The instrument, the subject of the present invention, allows to remedy these drawbacks.

With this in mind, the present invention relates to an instrument intended to remove parasitic ticks from the skin of animals or man, characterized by the fact that it consists of one piece provided, on the one hand, with a handle that ends in a round grip and, on the other hand, with a curved and flattened extremity that ends in a fork roughly perpendicular to the axis of rotation of said grip. This fork is formed by two prongs delimiting a so-called "prong interspace" intended for the gripping of the tick and suitable to remove the tick by rotating around a axis that is roughly perpendicular to the plane of the skin onto which the tick is adhered.

Owing to the present invention, the tick can be removed in a simple manner by inserting the prongs of the fork on one and the other side of the rostrum and by making the instrument rotate around an axis, so that the tick is neither squeezed nor lifted by simple traction but rather that it is essentially removed by rotation.

In accordance with the specific embodiments of the invention:

The two prongs can be provided with a trapezoid section in such a manner that the prong interspace presents a V-shaped vertical section, that would allow a better grip on the tick while it is being removed.

The prong interspace may be of variable width, in particular with an opening that would expand towards the free end of the fork, so that the instrument can be used for ticks of different sizes.

The free end of the two prongs can be chamfered and rounded.

The prongs of the fork may be rectilinear or they may be curved towards the handle.

The grip of the handle may be of larger diameter than that of the handle itself.

BRIEF DESCRIPTION OF THE DRAWINGS

The invention will be better understood and its other advantages will be seen more clearly through the below description of an embodiment of an instrument in accordance with its principle, given only by way of example and making reference to the accompanying illustrations wherein.

DESCRIPTION OF THE PREFERRED EMBODIMENT

Figure 1:
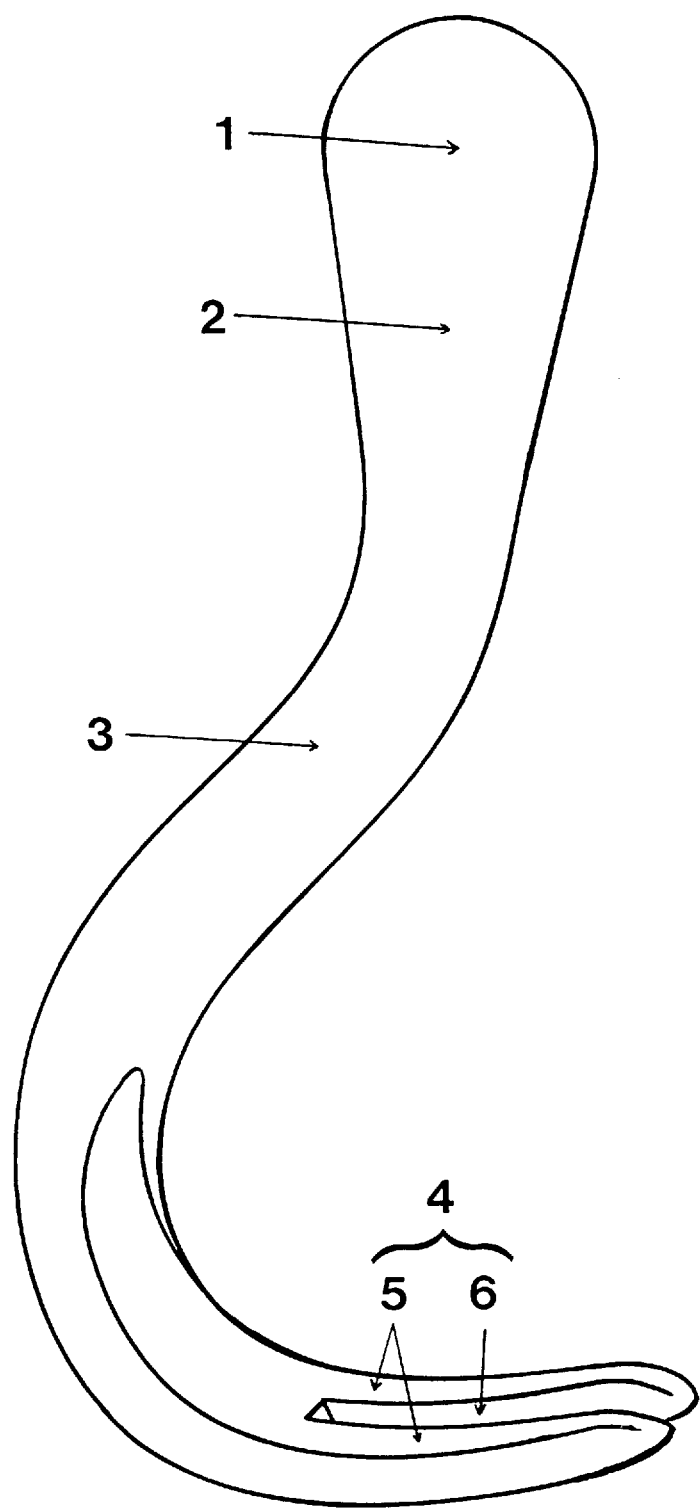
FIG. 1 is a perspective view of the instrument.
Figure 2:
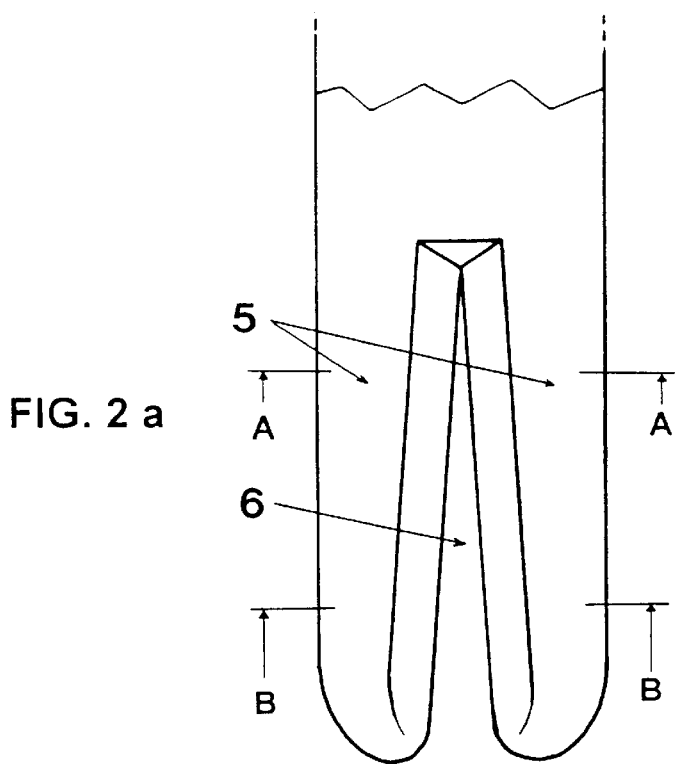
FIG. 2a is a top view of the fork and comprises two cross sections of this view.
FIG. 2b is a cross sectional view taken perpendicularly through the fork of FIG. 2a and along line A—A.
FIG. 2c is a cross sectional view taken perpendicularly through the fork of FIG. 2a and along line B—B.
Figure 2:
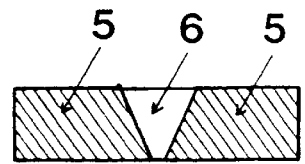
Figure 2:
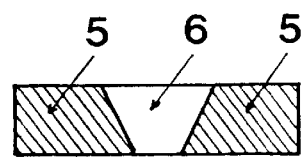
Figure 3:
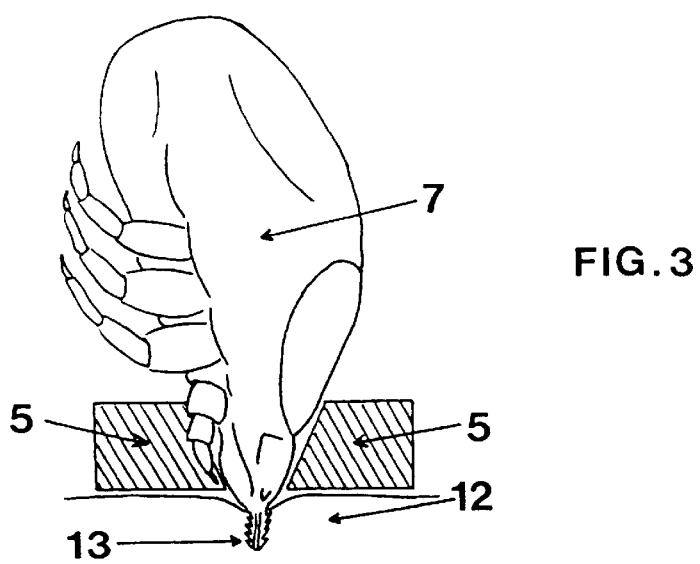
FIG. 3 shows the manner in which the tick is gripped and held.

The dimensions given by the scale are only by way of example but not limited to such.

With respect to the illustrations, the instrument comprises:

a hemispheric tip 1 and a truncated segment 2, that form the grip of the instrument;

a swan-necked handle 3 and a fork 4 constituted by two prongs 5 of trapezoid shape, separated by a "prong interspace" 6.

The prong interspace 6 presents a cross section in the shape of a vertical V, to fit around the head and the thorax of the tick 7, when the latter sticks to the skin 12. Thus, the tick's abdomen is not squeezed.

Figure 4:
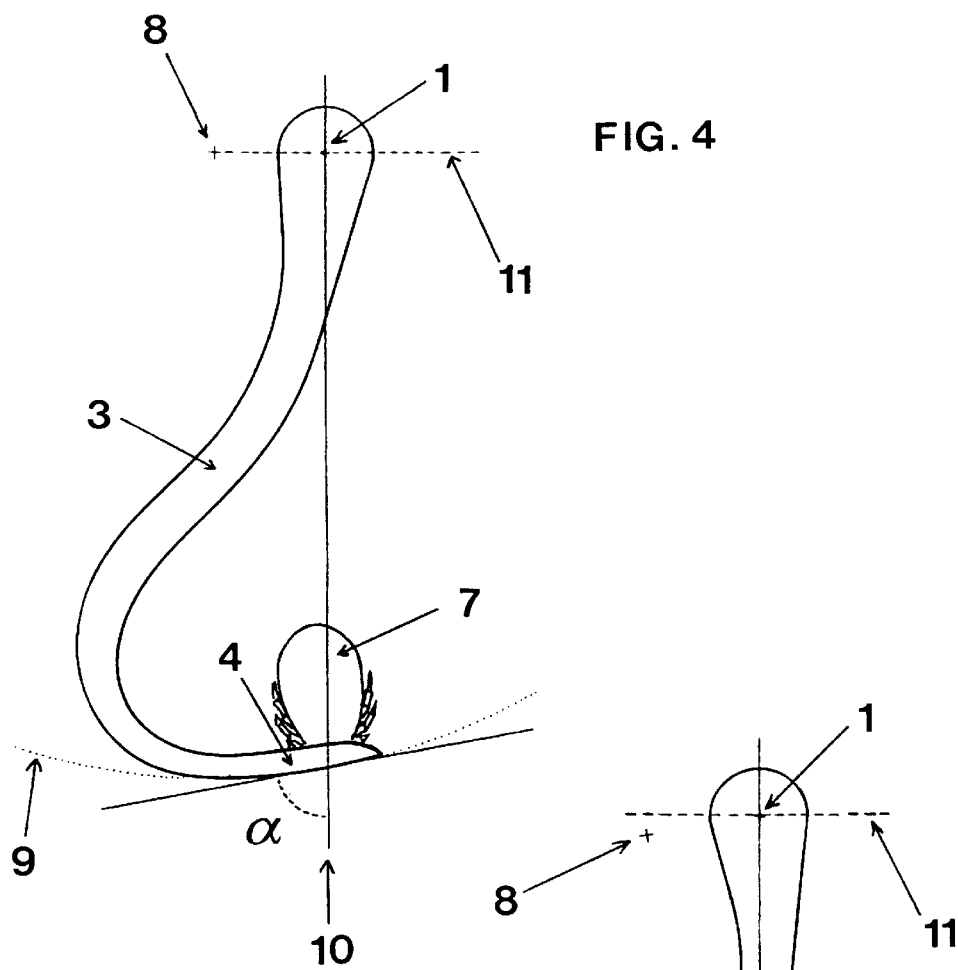
FIGS. 4 and 5 show two profile view of the instrument gripping ticks of different sizes.
Figure 5:
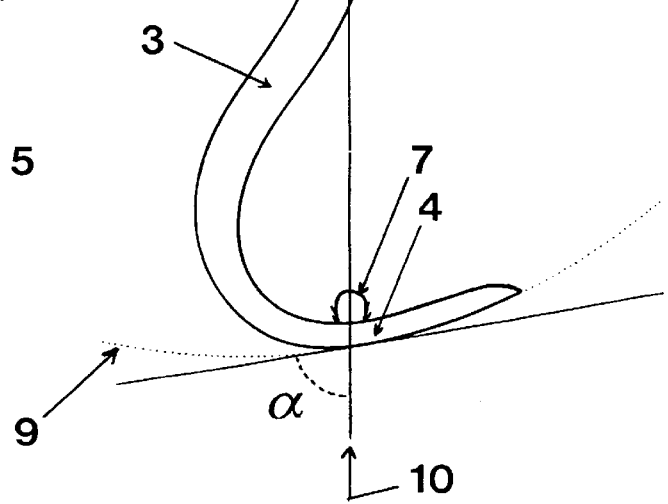

The opening of the prong interspace 6 widens towards the extremity, which makes it possible to firmly hold all ticks, regardless of their size. As a matter of fact, as it can be seen by comparing FIGS. 4 and 5, as regards the size of the tick, the fork holds more or less the tick on both sides. In the case of a large tick, as shown in FIG. 4, the tick is somewhat caught in the prong interspace 6, and the dimensions of the prong interspace, at the cross section B, make it possible not to squeeze the tick. In the case of a small tick, as shown in FIG. 5, the animal is deeply caught in the prong interspace 6 and can be firmly held in place because the prong interspace 6 is of relatively small dimensions as it can be seen in section A.

At the end of the fork 4, the top surfaces and the two lateral surfaces of each prong 5 are chamfered and the corresponding edges are rounded to facilitate the slipping of the fork 4 around both sides of the tick 7.

The axis of rotation 10 of the instrument can be defined as the axis passing through the center of the hemispheric tip 1 and the rostrum 13 of the tick 7. The axis 10 is roughly perpendicular to the plane of the skin onto which sticks the tick.

The center of the hemispheric tip 1 is set off forward with respect to the center 8 of a theoretical circle 9 into which would fit the prongs 5 of the fork 4, so that the axis of rotation 10 does always form an acute angle α of between 75° and 90° with the fork 4, whichever might be the position of the tick 7 in the fork 4.

The shape of the tip 1 of the instrument lets the operator place his fingers on the plane 11 perpendicular to the axis of rotation 10, whichever might be the position of the tick in the fork.

The instrument works as follows:

The operator holds the instrument by the truncated section of the handle. He nears the tick either on its right or its left side by placing the fork on the skin of the animal or man, the prongs directed towards the tick. He slides the fork underneath the tick by having the prongs gripping the parasite on both sides, until they come into close contact with it. He then exercises a slight pulling perpendicular to the skin in order to prevent the tick from escaping and rotates the entire instrument between the thumb and the index finger. Generally, the tick loosens after the second or third turn. The preliminary use of ether or of other acaricide products becomes superfluous.

The simplicity of the idea of the instrument allows to envisage its manufacture out of plastic, in one injection step, or out of cast metal. The instrument may be manufactured out of polyvinylacetal which presents the characteristic that it is resistant to alcohol or ether, which could be used to clean the instrument after its use or as an anaesthetic by a user who is accustomed to utilize such products.

What we claim is:

1. A method to remove parasitic ticks from the skin of animals or a person using an instrument including a fork having a pair of spaced prongs, including the steps of:

nearing a tick by placing the fork on the skin with the prongs of the fork being directed toward the tick;

sliding the fork across the skin such that the spaced prongs engage the tick on opposite sides thereof; and rotating the instrument around an axis that is generally perpendicular to a plane of the skin onto which the tick is attached to thereby remove the tick from the skin.

2. A method in accordance with claim 1, characterized by the additional step of exerting a pulling force generally perpendicular to the skin to prevent the tick from escaping prior to rotating the instrument.

3. An instrument for removing parasitic ticks from skin comprising, a body having a handle with a grip portion of generally circular cross section such that said grip portion is rotatable about an axis of said body extending generally perpendicularly through the circular cross section of said grip portion, said body including an extremity spaced from said grip portion ending in a fork which is oriented substantially perpendicularly to said axis, said fork having a pair of outwardly extending prongs defining a space therebetween, said prongs being adapted to extend generally parallel to the skin so as to engage a tick positioned within said space on opposite sides thereof and being rotatable relative to the skin when said grip portion is rotated about said axis to thereby extract the tick from the skin.

4. The instrument of claim 1 wherein each of said prongs is generally trapezoidal in cross section so that said space is generally V-shaped from an upper surface to a lower surface of each of said prongs.

5. The instrument of claim 4 wherein said prongs diverge outwardly relative to one another so that said space is of a varied width along at least a portion of a length of said prongs.

6. The instrument of claim 5 wherein said prongs include free ends which are chamfered so as to be inclined from said upper to said lower surfaces thereof.

7. The instrument of claim 6 wherein said body is integrally formed having an arcuate portion extending from said fork to said handle.

8. The instrument of claim 7 wherein said grip portion includes a truncated segment and a hemispherical tip.

9. The instrument of claim 3 wherein said body is integrally formed of a metal material.

10. The instrument of claim 3 wherein said body is integrally formed of a plastic material.

11. The instrument of claim 3 wherein said body is integrally formed having an arcuate portion extending from said fork to said handle.

12. The instrument of claim 3 wherein said prongs include free ends which are chamfered so as to be inclined from said upper to said lower surfaces thereof.

* * * * *